US005273044A

United States Patent [19]

Flusberg et al.

[11] Patent Number: 5,273,044

[45] Date of Patent: Dec. 28, 1993

[54] METHOD AND APPARATUS FOR NON-INVASIVE MEASUREMENTS OF SELECTED BODY ELEMENTS

[75] Inventors: Allen M. Flusberg; Ruth Shefer, both of Newton; Robert Klinkowstein, Winchester, all of Mass.; Mordechai Rokni, Mevaseret Zion, Israel

[73] Assignee: Science Research Laboratory, Inc., Somerville, Mass.

[21] Appl. No.: 684,393

[22] Filed: Apr. 12, 1991

Related U.S. Application Data

[63] Continuation-in-part of Ser. No. 488,300, Mar. 2, 1990, Pat. No. 5,135,704.

[51] Int. Cl.[5] ........................ A61B 5/00; G01N 23/06

[52] U.S. Cl. ........................ 128/659; 378/88; 128/653.1

[58] Field of Search ............... 128/653.1, 659; 378/86, 378/88; 250/363.01

[56] References Cited

U.S. PATENT DOCUMENTS

| | | | |
|---|---|---|---|
| 3,780,294 | 12/1973 | Sowerby | 250/269 X |
| 5,003,980 | 4/1991 | Loo et al. | 128/653.1 |
| 5,040,200 | 8/1991 | Ettinger et al. | 378/88 |
| 5,115,459 | 5/1992 | Bertozzi | 378/88 |

FOREIGN PATENT DOCUMENTS

| | | | |
|---|---|---|---|
| 9203722 | 3/1992 | European Pat. Off. | 378/86 |

*Primary Examiner*—Lee S. Cohen
*Assistant Examiner*—Krista M. Pfaffe
*Attorney, Agent, or Firm*—Wolf, Greenfield & Sacks

[57] ABSTRACT

A method and apparatus are provided for performing non-invasive measurements, and in particular in vivo non-invasive measurements of the total body content of a particular element, or of the content of such elemetn in a particular body area, by use of resonant gamma ray detection. More particularly, gamma rays are generated at the resonant gamma absorption energy level for the element on which measurements are to be made and are passed through the portion of the patient's body for which measurements are to be made. Detected gamma rays passing through the patient's body may be utilized as an indication of the content of such element. The effect of non resonant gamma absorption may be subtracted by also passing gamma rays of non-resonant absorption energy through the same body part and utilizing detected gamma rays at this energy passing through the body to determine the non-resonant absorptions.

24 Claims, 3 Drawing Sheets

METHOD AND APPARATUS FOR NON-INVASIVE MEASUREMENTS OF SELECTED BODY ELEMENTS

RELATED APPLICATIONS

This application is a continuation in part of application Ser. No. 07/488,300, filed Mar. 2, 1990, now U.S. Pat. No. 5,135,704.

FIELD OF THE INVENTION

This invention relates to medical diagnosis and treatment and more particularly to a method and apparatus for non-invasive, and generally in vivo, measurements of the quantity of a selected chemical or other element which is present in a patient's body or in a selected portion thereof.

BACKGROUND OF THE INVENTION

Patients can have increases or decreases in the percentage of certain chemicals or other elements, either throughout the body or in certain organs or other body parts, as a direct or indirect result of certain diseases. For example, osteoporosis, a widespread condition afflicting 15 to 20 million individuals in the United States alone, results from loss of mineral content of bone. As the bone loses mass and structural strength, the patient becomes susceptible to fractures. The principal mineral lost when osteoporosis occurs is calcium. Therefore, detection of calcium loss in bone should serve as a reliable indicator of osteoporosis.

However, current techniques for in vivo measurement generally measure bone mineral density rather than the fraction of body calcium in all or a portion of a patient's body. These technique include radiography of portions of the spinal column which, while readily available, is a crude measure, a loss of approximately 30% being necessary for osteoporosis to become evident by this technique. Other more sensitive techniques include radiogrammetry, photodensitometry, whole and partial body neutron activation, single and dual photon absorptometry, single and dual energy computed tomography and Compton scattering. Such measurements are made on part of the spine, the whole spine, the wrist, the hand or the heel, according to the technique used. While these techniques for measuring bone mineral density can be useful in the detection of, for example, osteoporosis, they also have a number of drawbacks.

One potential problem is that most of these techniques depend on the fact that bone absorbs certain radiations at a different rate than other portions of the body. However, for the current techniques, there are other portions of the body which absorb certain radiation at a rate which is not radically different from that of bone, resulting in potential errors in readings. For example, the percentage loss indicated by such techniques may be less than the actual percentage loss in bone density because the readings are picking up parts of the body, in addition to just bone.

A second potential problem is that the x ray or other radiation doses for all of the techniques are relatively high. For this reason, these techniques are generally performed on only a small portion of the body, an assumption being made that bone loss is uniform throughout the body. There is some controversy in the medical profession as to whether this is a valid assumption for all patients.

The relatively high doses also prevent the techniques from being used for early screening of patients, the techniques generally being used only for patients in high risk groups or where other indications exist that osteoporosis might be present.

The situation in detecting other elements in the body is even less advanced than that for calcium. For example, nitrogen is a major constituent (approximately 16%) of body protein, but is fractionally smaller in other body compartments. It may thus be possible to detect the mass of protein in a patient's body non-invasively from total body nitrogen measurements. Such total body nitrogen analysis can be used to monitor changes in body composition of cancer patients and assess the efficacy of various therapeutic regimens. Similarly, body composition measurements can be utilized to provide an understanding of AIDS-related malnutrition and to assess various nutritional therapies. Such techniques would also be useful in the diagnosis and treatment of other diseases which result in debilitation of the patient, and in particular in the debilitation of all or selected muscles of the patient or in nutritional debilitation.

Present non invasive methods for detecting a single element such as nitrogen in the body, such as those based on prompt-gamma neutron activation, monitor only the total body content of these elements, rather than their distribution throughout the body. Thus, serial measurements to monitor changes in total-body nitrogen do not reveal whether some fat-free tissue or particular organs gain or lose more protein than others. This may be undesirable since monitoring in vivo changes in the nitrogen content of individual organs or other body parts might lead to a better understanding of the mechanism of protein gain and loss and might be useful in diagnosing certain disorders, or the situs of certain disorders such as polio. However, present methods do not have the ability to determine element distributions because the required dosage would be to high.

This points up a second major disadvantage of existing techniques in that they require relatively high radiation doses, for example 27 mrem for a 1% accuracy in whole body measurement of nitrogen. This dosage is high enough so that measurements cannot be taken at frequent intervals to assess the effectiveness of a therapeutic regimen and screening tests would not be performed, tests only being performed when it is clear that a problem exists. Even when performed at infrequent intervals, tests performed at that radiation level can be potentially hazardous and would not normally be performed on, for example, young children or pregnant woman. As indicated above the radiation dosage required absolutely precludes the use of such techniques for localized nitrogen content assessment.

Other disadvantages of present chemical element detection techniques are the requirement of a radioactive source and the large size of the measurement system. Present use of radioactive plutonium as a source presents a security problem and requires extensive safeguards. It also presents a disposal problem for radioactive waste. Since a radioactive source cannot be turned off when not in use, heavy shielding must be provided which contributes to the size, weight and cost of such systems. Because of this and other factors, the large size of such measuring systems makes installation in a hospital unmanageable. As a result, clinical examinations using such equipment are currently limited to elaborate off-site facilities, rather than more appropriate hospital or health-care facilities located in or near population centers. The need to send patients to off site facilities, facilities which are frequently at some distance from the hospital where the patient is located, further increase the cost and inconvenience of using such equipment. As a result, the use of such equipment is not feasible for large classes of patients, including critically ill patients who are frequently the ones most in need of such testing.

A need therefore exists for an improved method and apparatus for performing non-invasive, and preferably in vivo, detection, and measurement of a single chemical or other element in a patient's body. Such technique should result in minimal radiation exposure so that tests may be utilized for screening, may be performed at frequent intervals to assess the efficacy of nutritional or other treatment regimen and may, in some instances, be utilized with young children, pregnant women and other potentially high risk classes of patients. Low dosage would also permit measurements to be made on selected body areas, in addition to total body measurements. The technique should also permit the body content of selected elements to be measured directly and should provide accurate indications of the content of such chemical element. Finally, the equipment should not require the use of a radioactive source, and it should be possible to fabricate the equipment for practicing the technique so that such equipment is small and inexpensive enough to be utilized at hospitals or other health care facilities where a need for such equipment exists.

SUMMARY OF THE INVENTION

In accordance with the above, this invention performs non-invasive measurements, and in particular in vivo non invasive measurements, of the total body content of a particular element or of the content of such element in a particular body area, by use of resonant gamma ray detection. In particular, the portion of the body on which the measurements are to be made is bombarded with gamma rays at the resonant gamma absorption energy for the particular element on which measurements are to be made. The resonant energy gamma rays which pass through the patient's body are detected and an indication of the content of the given chemical or other element in the portion of the patient's body through which the gamma rays were passed is obtained in response to the detected gamma rays. The resonant gamma rays are preferably obtained by bombarding a target with charged particles, for example, protons of a predetermined energy, the target being of a substance which produces gamma rays of the resonant energy at at least a selected angle with respect to the propagation direction of the charged particle beam when bombarded with such charged particles. The system passes only gamma rays at the selected angle through the body.

For preferred embodiments, the portion of the patient's body is also bombarded with gamma rays at a non-resonant energy level and the non-resonant gamma rays passing through the body are also detected. The detected non resonant gamma rays are then utilized to enhance the element content determination by eliminating therefrom the effect of non resonant attenuation. In particular, the enhancement is preferably effected by subtracting the resonant detected gamma rays from the non-resonant detected gamma rays after correcting for the difference in nonresonant attenuation at the two energies. For a preferred embodiment, the non-resonant gamma rays are obtained by permitting gamma rays at an angle slightly differing from the selected angle to pass through the portion of the patient's body, the angle being sufficiently different so that the gamma rays being passed are at a non-resonant energy, with either the resonant or non resonant gamma ray determination being stored and utilized with a current determination for the same body portion to eliminate the effect of non resonant attentuation at such body portion. The non resonant gamma rays may also be obtained by forming the target of a substance, in addition to the original substance, which, when bombarded with charged particles at the predetermined energy, produces gamma rays at the selected angle at a non resonant energy.

For a preferred embodiment, gamma rays at the selected angle are passed through the patient's body by providing a gamma ray shield positioned between the target and the patient's body, the shield having an opening therethrough at the selected angle to the target. All or a portion of the patient's body for which composition measurements are desired, are passed over the opening on the body side of the shield.

For preferred embodiments, the element being detected is either nitrogen or calcium. For nitrogen, the target substance is preferably $^{13}C$, the resonant gamma energy is approximately 9.175 MeV, the selected angle is 80.7°, the beam is a proton beam and the proton energy required is 1.7474 MeV. Where the chemical being detected is calcium, the target is preferably $^{39}K$, the resonant gamma energy is approximately 10.322 MeV, the selected angle is 80.4°, and the proton energy is 2.0429 MeV.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1:
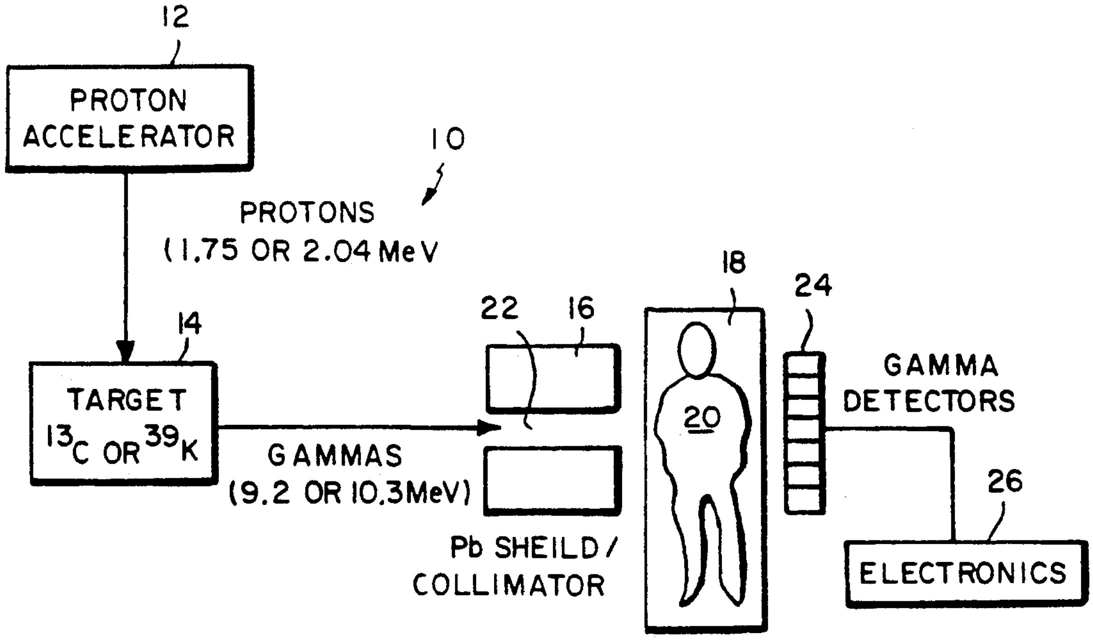
FIG. 1 is a schematic semi-block diagram of a system employing the teachings of this invention.

FIG. 1 illustrates a system which might be utilized to practice the teachings of this invention. While in the discussion to follow, it will be assumed that the chemical element being measured is either nitrogen or calcium, and these are the two elements for which use of the system is currently most suitable, it is to be understood that with suitable charged particles and particle energies from the accelerator, target compounds, and gamma ray energy and angle, the system could also be utilized to detect other body elements which are, for example, not as prevalent as nitrogen and calcium. Further, while in the discussion to follow reference is made to the measurement of nitrogen and calcium, for the specific examples given isotopes of these chemicals are actually being measured. For nitrogen, the isotope is $^{14}N$ which comprises 99.6% of the naturally occurring nitrogen in the body, and for calcium, the isotope is $^{40}Ca$ which comprises 96% of the naturally occurring body calcium. The system can extrapolate total nitrogen or calcium from measurements of these isotopes.

The system 10 shown in FIG. 1 includes a charged particle accelerator 12 which is preferably a proton accelerator and which, as will be described in greater detail in conjunction with FIG. 2, accelerates protons from an ion source to a required energy level and directs the high energy protons to a target 14. Where the substance being measured is nitrogen, the protons would be accelerated to approximately 1.7474 MeV and the target substance would be carbon 13 ($^{13}C$) Similarly, if the substance being detected is calcium, the protons would be accelerated to an energy level of 2.0429 MeV and would bombard a target of potassium 39 ($^{39}K$).

The target emits gamma rays in all directions with the energy of the emitted gamma rays differing slightly depending on the angle of the gamma rays to the bombarding proton beam. For nitrogen, the gamma resonant absorption energy level is approximately 9.17548 MeV and this energy level is obtained at an angle of approximately 80.7° from the protein beam direction. Similarly, for calcium, the gamma resonant absorption energy level is approximately 10.322 MeV, with gamma rays at this energy level being emitted from the $^{39}K$ target at an angle of approximately 80.4°.

A gamma ray shield 16, which may for example be formed of lead, is positioned between the gamma ray source (i.e. target 14) and scanning platform 18 o which the patient 20 is positioned. An opening 22 is provided in the shield which collimates the gamma rays and permits only gamma rays at the selected angle, and thus at the desired resonant energy level, to pass to patient 20.

Gamma rays at the resonant energy level which pass through the patient are detected by a bank of gamma ray detectors 24. The outputs from the gamma ray detectors are applied to a processor or other suitable device which is programmed to convert the detected gamma rays into a suitable indication of nitrogen or calcium content. Processing electronics 26 would include some form of output device or devices such as a printer, video display or the like which would provide an indication of whole body nitrogen or calcium content for the patient or, where measurements are being made on a selected one or more body portions, a printed or video graphic indication of the concentration of the detected element at such body location. The conversion from detected gamma rays to nitrogen or calcium content for a given system can be determined either mathematically or empirically and the electronics 26 programmed to generate suitable outputs in response to received levels of resonant gamma ray inputs. Electronics 26 may also control the sequencing and operation of the system, or other suitable control circuitry may be provided for this purpose with electronics 26 being synchronized with such circuitry. Electronics 26 may be special purpose hardware, but would normally be a programmed general purpose computing device of suitable speed and capacity. Most standard microprocessors or computer work stations should be adequate for performing the functions required of electronics 26.

Figure 2:
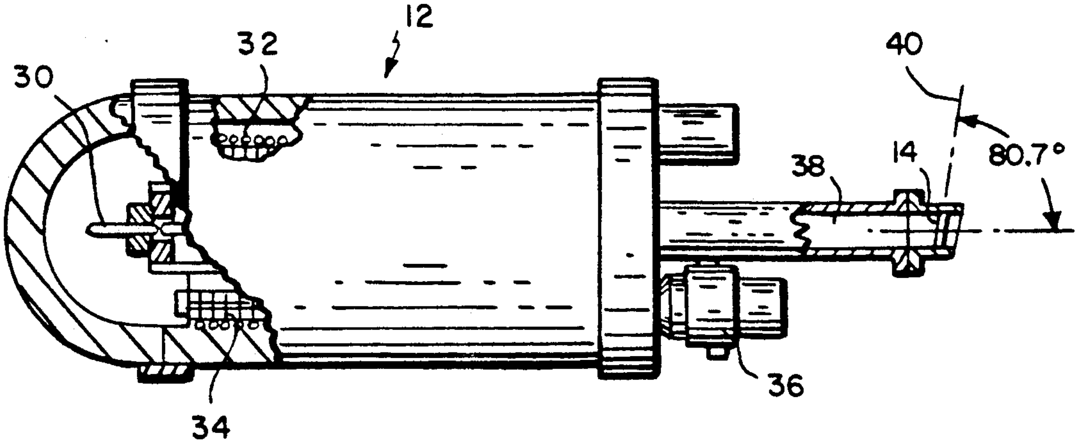
FIG. 2 is a cutaway side view of a proton accelerator and target suitable for use in the embodiment shown in FIG. 1 in practicing the teachings of this invention.

FIG. 2 shows one embodiment of a charged particle accelerator and target suitable for use as the elements 12 and 14 in FIG. 1. A device of the type shown in FIG. 2 is shown and described in greater detail in the before mentioned application Ser. No. 07/488,300, filed Mar. 2, 1990. Accelerator 12 consists of an RF ion source 30 of conventional construction which may, for example, be a generator producing an 80% monotonic deuteron beam having a power of approximately 2 to 4 KV at a current of up to 1 mA. Other ion sources might also be utilized. Ion source 30 is secured by an airtiqht seal to an accelerator tube 32, which may be a standard multi-electrode accelerator tube having a fixed interelectrode potential gradient. Ions from source 30 are applied to tube 32 and are accelerated thereby.

Accelerator tube 32 is surrounded by a symmetric cascade rectifier power supply or voltage multiplier 34 which may be of the type shown in co-pending application Ser. No. 07/488,744, filed Mar. 2, 1990 in the name of Robert Klinkowstein and assigned to the same assignee as this application. This cascade rectifier consists of a plurality of stages with equipotential plates between stages. The voltage gradient between the equipotential plates may be carefully controlled to provide a substantially uniform voltage gradient between plates and this gradient is selected to be substantially equal to the voltage gradient along the corresponding section of accelerator tube 32. This matching of voltage gradients significantly enhances the operating efficiency of the system. The accelerator mechanism is described in substantially greater detail in the two before mentioned co-pending applications. Accelerator tube 32 is maintained under vacuum by a vacuum pump 36 as is a channel 3 which extends from the end of the accelerator tube to target 14. As previously indicated, gamma rays are emitted from target 14 at all angles, with the gamma rays 40 being emitted at a selected angle, for example, 80.7° where nitrogen is the element being measured, being at the gamma resonant absorption energy level for the chemical being measured.

Another charged particle accelerator suitable for use as the element 12 in FIG. 1 is shown in U.S. Pat. No. 4,812,775 issued Mar. 14, 1989 and entitled "Electrostatic Ion Accelerator". This accelerator is a tandem accelerator with negative ions generated by a high current negative ion source being accelerated by an electrostatic accelerator in which the high voltage is produced by a solid state power supply. The solid state power supply is preferably a cascade rectifier power supply which is coaxial with either of the two tandem accelerator tubes to which the accelerated ions are applied. The stripping cell removes electrons from the ions, converting them into positive ions. The positive ions are then accelerated to a target which is preferably at ground potential. The cascade rectifier is preferably designed to have a voltage gradient which substantially matches the maximum voltage gradient of the accelerator. A more detailed description of this tandem accelerator is provided in the patent mentioned above.

Figure 3A:
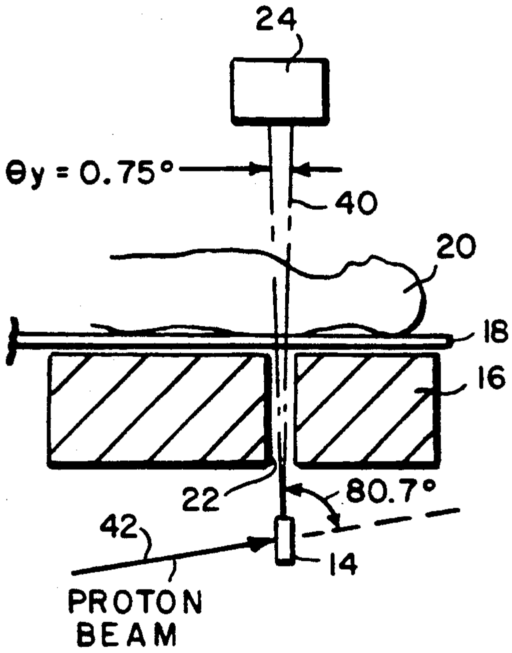
FIG. 3A and FIG. 3B are a side view and front view, respectively, of a gamma ray shield, scanning platform and detector suitable for use in practicing the teachings of this invention.
Figure 3B:
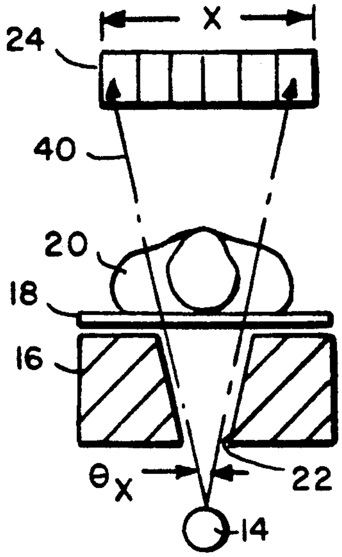

FIGS. 3A and 3B illustrate in greater detail the manner in which gamma ray beam 40 at the desired energy level is collimated and applied to the patient. Referring to these figures, the proton beam 42 applied to target 14 results in a gamma ray beam 40 at the desired angle. All gamma rays except the gamma rays at the desired angle, and thus the desired energy level, are blocked by shield 16, gamma rays of the desired energy level passing through opening 22 in the shield. The gamma rays passing through opening 22 also pass through scanning platform 18 and the desired area of the patient s body to be received by gamma ray detectors 24.

From these figures, it is seen that the beam diverges in both the side and front dimension as it passes from target 14 to detectors 24. For a typical detector with X=to 30 centimeters and a distance from target 14 to patient 20 which is also equal to 30 centimeters, the angle $\theta x$ shown in FIG. 3B would typically be limited to 1 rad (i.e. 57°). The angle $\theta y$ is determined to some extent by the desired resolution. For a preferred embodiment, this angle is approximately 0.75°. Factors in determining this angle are discussed later.

Where whole body scanning is being performed, scanning platform 18 may be moved continuously at a rate such that each part of the body being scanned receives the required radiation dosage as such body part passes over opening 22. Alternatively, a single line can be irradiated and platform 18 then incrementally moved in the "y" direction a small distance to irradiate the next section of the body, the steps being small enough so that all parts of the body are irradiated with little or no overlap.

Figure 5:
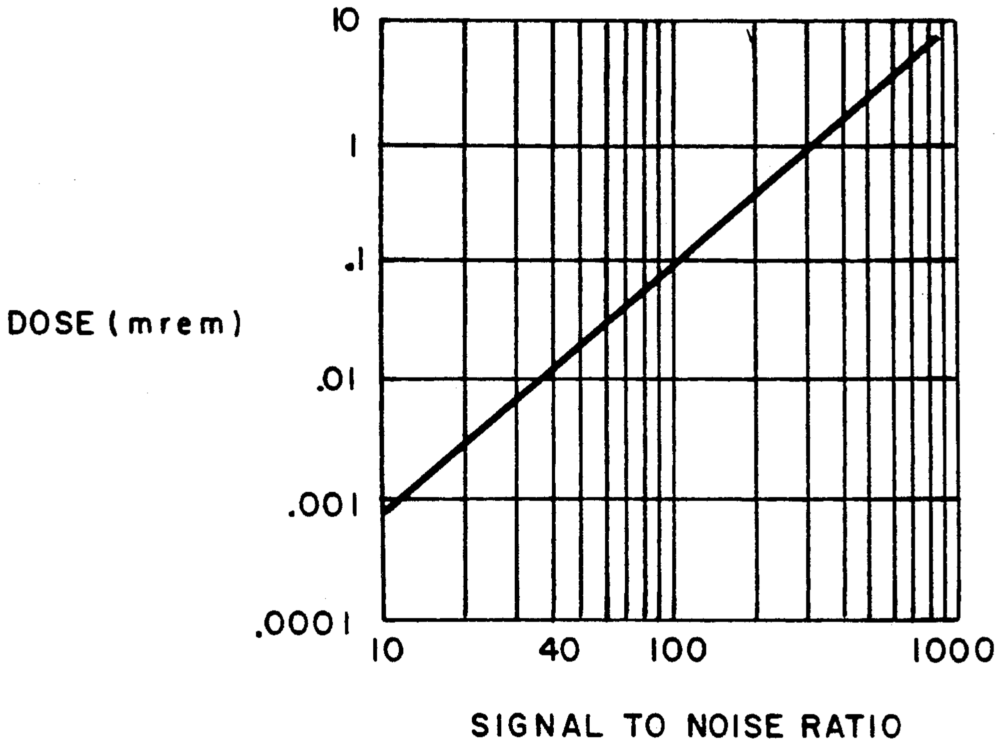
FIG. 5 is a graph illustrating the relationship between signal to noise ratio (or desired accuracy which is reciprocal of signal-to-noise ratio) and required dosage of gamma rays for a whole-body measurement of either nitrogen or calcium.

As is shown in FIG. 5, the gamma ray dosage required increases with the desired signal to noise ratio, signal-to-noise ratio being a measure of accuracy. Thus, for a whole body measurement of either nitrogen or calcium, with an error of approximately 2% (i.e. 98% accurate), which corresponds to a signal to noise ratio of approximately 40, a gamma ray dosage of approximately 0.02 mrem is required. This is approximately the same dose obtained by the average person from background radiation every half hour. The time required to make such a measurement with a 5 mA proton accelerator 12 is approximately 3.6 minutes. Similarly, the dosage required to determine whole body nitrogen or calcium content to a 99% accuracy level (i.e. 1% inaccuracy or error) is approximately 0.08 mrem (this corresponds to a signal to noise ratio of approximately 100 in FIG. 5). This, again, is equal to the background radiation which a patient would normally receive over two hours, and is approximately 0.3% (i.e. about 1/300) of the 27 mrem required for comparable accuracy using prompt-gamma neutron activation. This low dosage permits measurements to be taken (a) for diagnostic screening, (b) at relatively frequent intervals to assess the efficacy of nutritional or other treatment regimens, and (c) on high risk patients. It also permits the technique to be utilized to perform imaging of, for example, nitrogen or calcium content in a particular area of the body. The advantages of being able to map in a particular body area has been previously discussed.

In particular, it is possible to obtain images of calcium or nitrogen content with a resolution of approximately 2 centimeters by displacing the body portion of interest in the manner previously described in front of gamma ray beam 40. Since the dose received by the body is proportional to the number of gamma ray photons ($n_o$) incident over a cross sectional area (A) (i.e. dose $\propto n_o/A$), and since $n_o$ remains substantially constant for a given accuracy regardless of the size of the body area being scanned, the dosage increases as the area being scanned decreases. Thus, the dosage required for a whole-body assessment is, as indicated above, exceedingly low. For a body thickness of 30 centimeters, a radiation area of 7500 $cm^2$ and a whole body nitrogen content of 2.5%, these being fairly typical figures, the dose is only 0.08 mrem for a signal-to-noise (S/N) ratio of 100 (see FIG. 5). This provides a measurement accuracy of 0.025% nitrogen. For a 2 centimeter resolution over a region of the body which is 30 centimeters thick, a dose of 24 mrem is adequate to attain a nitrogen content accuracy of 0.06% (corresponding to an S/N ratio of approximately 40). Thus, the resonant gamma ray absorption technique of this invention is capable of giving 2 centimeter resolution of nitrogen distribution at a dose which is less than that currently required for a whole body measurement. Such resolution thus becomes feasible for the first time.

However, a potential problem with the technique of this invention is that the element being measured makes up a very small percentage of the body. Thus, while the element absorbs gamma rays at the resonant energy level strongly, there is also substantial non resonant attenuation of these gamma rays (predominantly Compton scattering and pair production). Since the chemical being measured makes up only a small portion of the body, about 2.5% for nitrogen or calcium (with most of the body consisting of water), the non resonant attenuation may be 40 times the resonant absorption, thus masking the effect of such absorption and substantially reducing the resolution of the system.

To overcome this problem, it is necessary to enhance the imaqe by determining the non resonant attenuation of gamma rays in the area being scanned and compensating for such attenuation. The determination of non resonant attenuation of the gamma rays may be accomplished in a number of ways.

One way in which to determine non resonant attenuation is to utilize a composite target 14 which is formed both of the substance required to generate the resonant gamma rays and of a substance which produces non resonant gamma rays of a selected energy which is reasonably close to the energy of the resonant gamma rays at the angle of opening 22 when bombarded by proton beam 42 at the energies previously discussed. The gamma ray detectors 24 would need to provide energy resolution in order to distinguish between the gamma rays at the two different energies. A problem with this approach is the difficulty of finding a suitable substance to produce non resonant gamma rays at an energy level close enough to that of the resonant gamma rays, while simultaneously far enough away to allow the detectors 24 to distinguish between them so that information on non-resonant attenuation can be extracted and utilized without introducing systematic errors.

Figure 4:
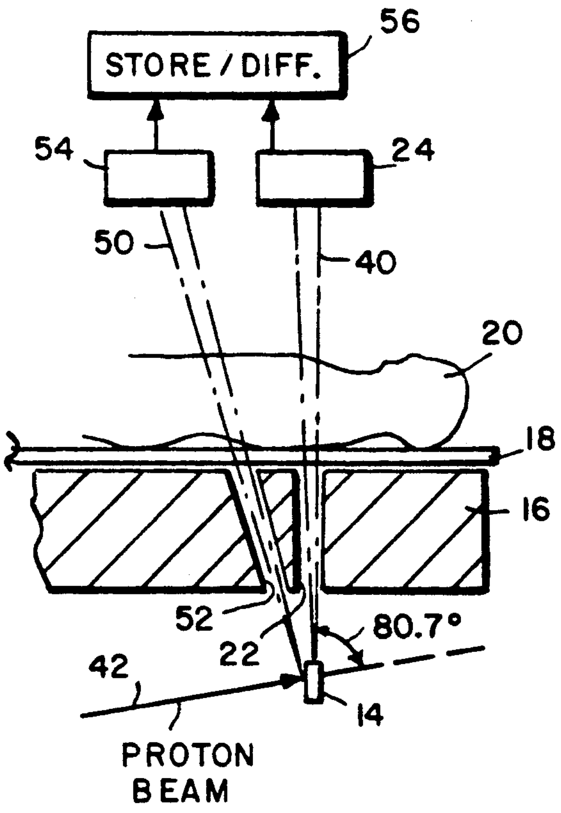
FIG. 4 is a side view of an alternative embodiment for the shield scanning platform and detector.

FIG. 4 illustrates another way in which non resonant gamma ray determinations may be made. As was previously indicated, while gamma rays are emitted in all directions from target 14, the energy level of the gamma rays differs at different angles. Thus, gamma rays 50 passed through an opening 52 in shield 16, which opening is displaced slightly from opening 22, would be at a different predictable energy level which could be detected by a suitable detector 54. A 3° displacement between the angles of beams 40 and 50 should provide adequate energy differences to permit a non-resonant attenuation determination to be made for most elements, although some experimentation may be required to determine an optimum angle for this purpose in a particular application.

The outputs from detectors 24 nd 54 could be applied to a store and difference circuit 56 which would store the reading taken by detector 24 during a given cycle and then subtract this value from the reading taken at the same point on the patient's body by detector 54 during the next cycle (or during a predetermined subsequent cycle if the spacing between the detectors is more than that covered during a single incrementing of platform 18), so that the two inputs being subtracted or otherwise processed are for the same point on the patient's body. Since the difference in gamma ray attenuation at detectors 24 and 54 is the additional resonant gamma ray attenuation, this subtraction eliminates the effect of non resonant absorption and, after a small adjustment to account for the difference in body thickness seen by the two beams, leaves a signal which is proportional to the resonant absorption of gamma rays by the element being measured. This permits high resolution outputs to be obtained. The nonresonant absorption correction would normally be required whether doing whole body or localized measurements.

In the discussion above, various values have been given for parameters such as proton beam energy, collection angle for gamma rays from the target and resonant gamma ray energy. Some of these values are carried out to a number of decimal places. However, there are several factors which influence each of these values. For example, because the incident proton beam momentum upshifts gamma rays slightly, the exact output energy of the gamma rays depends, as previously indicated, on the angle $\alpha_0$ between the emission direction of the gamma rays and the incident proton beam. In order for the emitted gamma rays to be at a proper energy level, the energy of the proton beam must precisely match the transition energy required to produce the desired gamma rays corrected for the recoil of the target substance resulting from the Doppler effect. Some small variations in energy in the range of approximately 200 eV may be permitted while still obtaining satisfactory results. However, it has been found that it is not necessary for the proton beam incident on the target to be tuned within the tolerance indicated above; but it is only necessary that the proton beam energy be slightly above resonance. When protons penetrate the target, they lose energy by collision. Consequently, they will be tuned to resonance by the target itself.

The second condition is that only useful gamma rays emitted at or near the proper angle $\alpha_0$ be utilized. To maximize the resonant absorption of gamma rays by the element being tested for, the energy spread of the gamma rays should be kept within the resonance linewith for the element which is approximately 135 eV for $^{14}N$. Mechanisms which contribute to this energy spread are the angular width $\Delta\alpha$ of the collected gamma ray beam. It is, therefore, desirable to hold $\Delta\alpha$ as small as possible. However, because of the Doppler effect, many resonant gamma protons are emitted at angles outside theoretical angles, and it has been experimentally determined that the previously indicated angular divergence of 0.75° is acceptable.

While the invention has been particularly shown and described above with reference to specific applications and specific hardware configurations, it is apparent that other suitable components could be substituted for various components described herein and that the invention could be utilized in practicing other applications. For example, while accelerator 12 has been indicated as a proton accelerator for preferred embodiments, ions or other charged particles may be accelerated for other elements or applications.

Thus, the foregoing other changes in form and detail may be madein this invention by one skilled in the art while still remaining within the spirit and scope of the invention.

What is claimed is:

1. A system for performing non-invasive composition measurements of a predetermined element in at least a portion of a patient's body comprising:

a target of a substance which, when bombarded with selected charged particles at a predetermined energy, produces gamma rays at at least a selected angle of an energy which is equal to the resonant gamma absorption energy of the element;

means for bombarding the target with the charged particles at said predetermined energy to generate gamma rays;

means for permitting gamma rays at said selected angel to pass through at least the portion of the patient's body for which composition measurements are desired;

means for detecting gamma rays of said resonant energy passing through the patient's body; and means responsive to the detected gamma rays for determining the composition of said element in the portion of the patient's body through which the gamma rays were passed.

2. A system as claimed in claim 1 wherein there is also non-resonant attentuation of gamma rays in said body portion, including means for also bombarding the portion of the patient's body with gamma rays at a non resonant energy level;

means for detecting non resonant gamma rays passing through the body; and enhancement means responsive to the non resonant detecting means for eliminating the effect of non resonant attenuation from the determination of element composition.

3. A system as claimed in claim 2 wherein said enhancement means subtracts the resonant detected gamma rays from the non-resonant detected gamma rays to determine the resonant gamma ray absorption.

4. A system as claimed in claim 2 wherein the non resonant energy bombarding means includes means for permitting gamma rays at an angle slightly differing from said selected angle to pass through the portion of the patient's body, the angle being sufficiently different so that the gamma rays passed are at the non-resonant energy level; and wherein said enhancement means includes means for storing either resonant or non resonant determinations, and means for utilizing the stored determination and the current determination for the non stored items for the same body portion to eliminate the effect of non resonant attenuation at such body portion.

5. A system as claimed in 2 wherein the non-resonant energy bombarding means includes said target being formed of said substance and also of a substance which, when bombarded with charged particles at said predetermined energy, produces gamma rays at said selected angle of the non-resonant energy level.

6. A system as claimed in claim 1 wherein said means for permitting includes a gamma ray shield positioned between said target and the patient's body, said shield having an opening therethrouqh at the selected angle to the target, whereby only gamma rays at said resonant energy level pass through said shield.

7. A system as claimed in claim 6 wherein said means for permitting includes means adapted for passing the portion of the patient's body for which composition measurements are desired past the opening on the body side of the shield.

8. A system as claimed in claim 1 wherein said element is nitrogen, said target substance is $^{13}C$, said resonant gamma energy is approximately 9.175 MeV, and the selected angle is 80.7°.

9. A system as claimed in claim 8 wherein said element is $^{14}N$, wherein said resonant energy is 9.17548 MeV, and wherein said charged particles are protons, having predetermined energy of 1.7474 MeV.

10. A system as claimed in claim 1 wherein said element is calcium, said target substance is $^{39}K$, said resonant gamma energy is approximately 10.322 MeV, and the selected angle is 80.4°.

11. A system as claimed in claim 10 wherein said element is $^{40}Ca$, and wherein said charged particles are protons having a predetermined energy of 2.0429 MeV.

12. A system as claimed in claim 1 wherein the measurements of said element are being made for the patient's total body, and wherein said means for permitting permits the gamma rays to pass through the patient's total body.

13. A method for performing non-invasive composition measurements of a predetermined element in at least a portion of a patient's body comprising the steps of:

bombarding a target of a selected substance with charged particles of a predetermined energy to generate gamma rays of an energy at at least a selected angle which is equal to the resonant gamma absorption energy of the element;

permitting gamma rays at said selected angle to pass through the portion of the patient's body for which composition measurements are desired;

detecting gamma rays of said resonant energy passing through the patient's body; and determining, in response to the detected gamma rays, the composition of said element in the portion of the patient's body through which the gamma rays were passed.

14. A method as claimed in claim 13 including the steps of: bombarding the portion of the patient's body with gamma rays at a non-resonant energy level;

detecting the non-resonant gamma rays passing through the body;

determining non resonant attenuation of gamma rays in said body portion in response to the non-resonant detection and utilizing the non-resonant attenuation determination to eliminate the effect of non resonant attenuation from the element composition determination.

15. A method as claimed in claim 14 wherein said utilizing step includes the step of subtracting the resonant detected gamma rays from the non resonant detected gamma rays to determine the resonant gamma ray absorption.

16. A method as claimed in claim 14 wherein the non-resonant energy bombarding step includes the step of permitting gamma rays at an angle slightly differing from said selected angle to pass through the portion of the patient's body, the angle being sufficiently different so that the gamma rays passed are at a non-resonant energy; and wherein said utilizing step includes the steps of storing either resonant or non resonant determinations, and utilizing the stored determination and the current determination for the non-stored item for the same body portion to eliminate the effect of non resonant attenuation at such body portion.

17. A method as claimed in 14 wherein said target is a composite target formed of said substance and also of a substance which, when bombarded with charged particles at said predetermined energy, produces gamma rays at said selected angle which are at a non-resonant energy, the non resonant energy bombarding step including the step of bombarding the composite target with charged particles at said predetermined energy.

18. A method as claimed in claim 13 wherein said permitting step includes the step of positioning a gamma ray shield between said target and the patient's body, said shield having an opening therethrough at the selected angle to the target, whereby only gamma rays at said resonant energy level pass through said shield.

19. A method as claimed in claim 18, wherein said permitting step includes the step of providing apparatus adapted to pass the portion of the patient's body for which composition measurements are desired past the opening on the body side of the shield.

20. A method as claimed in claim 13 wherein said element is nitrogen, said target substance is $^{13}C$, said resonant gamma energy is approximately 9.175 MeV, and the selected angle is 80.7°.

21. A method as claimed in claim 20 wherein said element is $^{14}N$ wherein said resonant energy is 9.17548 MeV, and wherein said charged particles are protons at a predetermined energy of 1.7474 MeV.

22. A method as claimed in claim 13 wherein said element is calcium, said target substance is $^{39}K$, said resonant gamma energy is approximately 10.322 MeV, and the selected angle is 80.4°.

23. A method as claimed in claim 22 wherein said element is $^{40}Ca$, and wherein said charged particles are protons at a predetermined energy of 2.0429 MeV.

24. A method as claimed in claim 13 wherein the measurements of said element are being made for the patient's total body.

* * * * *